United States Patent [19]

Mowrey-McKee et al.

[11] Patent Number: 5,422,073
[45] Date of Patent: Jun. 6, 1995

[54] METHOD AND COMPOSITION FOR DISINFECTING CONTACT LENSES

[75] Inventors: Mary Mowrey-McKee, Naperville; Kenneth Bliznik, Lansing; Ralph Stone, Naperville, all of Ill.

[73] Assignee: Allergan, Inc., Irvine, Calif.

[21] Appl. No.: 78,164

[22] PCT Filed: Dec. 18, 1991

[86] PCT No.: PCT/US91/09185

§ 371 Date: Jun. 17, 1993

§ 102(e) Date: Jun. 17, 1993

Related U.S. Application Data

[63] Continuation-in-part of Ser. No. 634,994, Dec. 27, 1990, abandoned.

[51] Int. Cl.⁶ .................... A61L 2/00; A61L 2/16
[52] U.S. Cl. .................... 422/28; 134/901; 424/78.26; 424/78.36; 514/839; 514/840
[58] Field of Search .................... 422/28; 134/901; 424/78.36, 78.26; 514/669, 839, 840

[56] References Cited

U.S. PATENT DOCUMENTS

| | | | |
|---|---|---|---|
| 3,908,680 | 9/1975 | Krezanoski | 134/27 |
| 4,058,624 | 11/1977 | Jacobus et al. | 424/330 |
| 4,312,833 | 1/1982 | Clough et al. | 422/30 |
| 4,367,157 | 1/1983 | Sherman | 252/106 |
| 4,395,346 | 7/1983 | Kleist | 252/135 |
| 4,454,151 | 6/1984 | Waterbury | 424/78.26 |
| 4,465,770 | 8/1984 | Madrovich | 435/12 |
| 4,490,389 | 12/1984 | Nelson et al. | 422/28 |
| 4,581,379 | 4/1986 | Nelson et al. | 514/840 |
| 4,758,595 | 7/1988 | Ogunbiyi et al. | 424/78.26 |
| 4,829,083 | 5/1989 | Doulakas | 514/496 |
| 4,836,986 | 6/1989 | Ogunbiyi | |
| 4,921,544 | 5/1990 | Cowle et al. | 134/901 |
| 4,960,799 | 10/1990 | Nagy | 514/567 |
| 5,246,552 | 9/1993 | Kamiya et al. | 204/131 |

FOREIGN PATENT DOCUMENTS

| | | |
|---|---|---|
| 0565948 | 5/1985 | Australia. |
| 0306984 | 3/1989 | European Pat. Off. ........ A61K 9/06 |
| 0575290A1 | 12/1993 | European Pat. Off. |
| 1246841 | 9/1971 | United Kingdom. |
| 1432345 | 4/1976 | United Kingdom. |
| WO9101763 | 2/1991 | WIPO. |
| WO9117469 | 11/1991 | WIPO. |

OTHER PUBLICATIONS

Neidhardt (Ed) Escherignia Coli and Salmonella Typhimyrium, vol. 1 (1987) pp. 7–22 American Society of Microbiology.

McCray et al.; Journal of Clinical Microbiology Oct. 1986 pp. 625–628.

Merck Index, 11th ed. p. 1395–entry 9575 "Tromethamine" (1989).

CTFA Cosmetic Ingredient Dictionary, Estrin et al, Third Edition, no date available.

Angus Chemical Company Technical Bulletin "Tris Amino", Apr. 1989.

Reinhardt et al, ICLC, vol. 17, Jan./Feb. 1990.

Chemical Abstracts 99: 93804 X, Abstracting, FR 2,517,208 by Andermann et al (Jun. 3, 1983).

Primary Examiner—Robert J. Warden
Assistant Examiner—Krisanne M. Thornton
Attorney, Agent, or Firm—Frank J. Uxa

[57] ABSTRACT

The present invention covers a method for disinfecting a contact lens including contacting the lens with an isotonic aqueous solution comprising 0.6 to 2 weight percent tromethamine (preferably 0.8 to 1.5 percent) for a time sufficient to disinfect the lens. Other aspects include adding to the solution from 0.01 to 1 weight percent chelating agent (preferably disodium EDTA) and/or additional microbicide.

20 Claims, No Drawings

METHOD AND COMPOSITION FOR DISINFECTING CONTACT LENSES

This application is a continuation-in-part of application Ser. No. 07/634,994, filed Dec. 27, 1990, now abandoned.

A disinfectant for soft contact lenses must have, in combination, the following properties:
 (1) it must perform the required disinfection, and
 (2) it must be harmless to soft contact lenses, and
 (3a) any remaining on the lens after disinfection must be harmless to the eye of the contact lens wearer or
 (3b) it must be capable of being neutralized to a harmless form prior to the wearer's use of the lens.

Three percent hydrogen peroxide adequately fulfills (1), (2) and (3b). However, the neutralization step is considered undesirable by many users. Hence, it is far more desirable to have a disinfectant that fulfills (1), (2) and (3a).

International Patent Publication No. WO 91/01763 discloses that solutions having very low concentrations of peroxide, i.e., from 0.01 to 0.5 percent more preferably 0.05 to 0.2 percent can provide disinfection without requiring neutralization. Use of the present invention greatly enhances the microbicidal efficacy of peroxide in such low concentrations.

U.S. Pat. No. 4,758,595 (Ogunbiyi, et al.) discloses that polyhexamethylene biguanide (PHMB) and its water-soluble salts can fulfill minimal disinfection and be harmless to the eye and the lens, if used with a specific buffer, a surfactant, and in specific concentrations.

The present invention, in its preferred aspects, has superior disinfection properties and is substantially non-irritating as observed clinically. The present invention is based upon the surprising finding that tromethamine and its salts, in proper concentration, is a bactericide and fungicide. Furthermore, tromethamine has a synergistic effect when combined with other known microbicides and chelating agents.

The present invention may be summarized as a method for disinfecting a contact lens comprising contacting the lens with an isotonic aqueous solution comprising 0.6 to 2 weight percent tromethamine (preferably 0.8 to 1.5 percent) for a time sufficient to disinfect the lens. Other aspects include adding to the solution from 0.01 to 1 weight percent chelating agent (preferably disodium EDTA) and/or additional microbicide, (preferably 0.00001 to 0.1 or 0.00001 to 0.01 ) weight percent PHMB, N-alkyl-2-pyrrolidone, chlorhexidine, polyquaternium-1, hexetidine, bronopol, alexidine, low concentrations of peroxide, and ophthalmologically acceptable salts thereof.

The term "ophthalmologically acceptable" when used to describe salts, etc. in this specification and claims is intended to mean a compound which is soluble in the solution at its effective concentration and will not harm the eye or the lens. Examples of ophthalmologically acceptable ingredients are given throughout the specification. Of course, use of other ophthalmologically acceptable ingredients is within the scope of this invention.

The present invention has the advantage of providing a method and a composition for disinfecting contact lenses for a wide range of microorganisms such as *Fusarium solani, Aspergillus fumigatus, Staphylococcus epidermidis, Pseudomonas aeruginosa, Serratia marcescens, Candida albicans,* and *Herpes simplex.* Of these, disinfecting of *S. marcescens* and *C. albicans* on lenses has proven particularly difficult with prior art compositions. The present invention also has the advantage of providing a method and a composition for disinfecting contact lenses which is compatible with, and has little or no undesirable chemical reactions with hydrophilic contact lenses. Another advantage of the present invention is that it provides a method and a composition for disinfecting contact lenses which has a low potential for irritating the eyes, And still yet another advantage of the present invention is that in certain embodiments, it provides a method and composition for disinfecting contact lenses, for cleaning tear film debris from contact lenses, and for lubricating contact lenses.

Tromethamine, whose chemical name is 2-amino-2-hydroxymethyl-1,3-propanediol, is also known by names of trimethylol aminomethane; tris(hydroxymethyl)aminomethane; trisamine; tris buffer; trometamol; Tromethane; THAM; TRIS; Talatrol; Tris Amino; Tris-steril; Trizma as described in the Merck Index, Eleventh Edition, Published by Merck & Co., Inc. Rahway, N.J. (1989). Tromethamine and its salts act as buffers over the pH range of 6–9. In the ANGUS Chemical Company Technical Bulletin TB 69, TRIS AMINO ® as a buffer for pH control, Angus Chemical Company it is disclosed that TRIS AMINO holds the pH of contact lens cleaning solutions in the range most favorable for hydrolysis of protein films on lens surfaces, and that the lack of eye irritancy of TRIS AMINO are of prime consideration in its choice for this application. However the ANGUS technical bulletin fails to disclose use of tromethamine in formulating contact lens disinfecting solutions, the fact that tromethamine has microbicidal properties, nor the fact that tromethamine has a synergistic effect when combined with other microbicides.

Ophthalmologically acceptable chelating agents useful in the present invention include amino carboxylic acid compounds or water-soluble salts thereof, including ethylene diamine tetraacetic acid, nitrilo triacetic acid, diethylene triamine pentaacetic acid, hydroxyethyl ethylene diamine triacetic acid, 1,2-diaminocyclohexane tetraacetic acid, ethylene glycol bis (beta-aminoethyl ether) in N, N, N', N' tetraacetic acid (EGTA), amino diacetic acid and hydroxyethyl amino diacetic acid. These acids can be used in the form of their water soluble salts, particularly their alkali metal salts. Especially preferred chelating agents are the di-, tri- and tetra-sodium salts of ethylene diamine tetraacetic acid (EDTA), most preferably disodium EDTA (Disodium Edetate).

Other chelating agents such as citrates and polyphosphates can also be used in the present invention. The citrates which can be used in the present invention include citric acid and its mono-, di-, and tri-alkaline metal salts. The polyphosphates which can be used include pyrophosphates, triphosphtes, tetraphosphates, trimetaphosphates, tetrametaphosphates, as well as more highly condensed phosphates in the form of the neutral or acidic alkali metal salts such as the sodium and potassium salts as well as the ammonium salt.

The pH of the solutions should be adjusted to be compatible with the eye and the contact lens, such as between 6.0 to 8.0, preferably between 6.8 to 7.8 or between 7.3 to 7.7. Significant deviations from neutral (pH=7) will cause changes in the physical parameters (ie. diameter)in some contact lenses. Low pH (pH less than 5.5) can cause burning and stinging of the eyes, while very low or very high pH (less than 3.0 or greater than 10) can cause ocular damage.

The term "disinfect" means the rendering non-viable of substantially all pathogenic microbes that are in the vegetative state, including gram negative and gram positive bacteria, as well as fungi.

The additional microbicides employed in the present invention are known, such as polyhexamethylene biguanide, N-alkyl-2-pyrrolidone, chlorhexidine, polyhexamethylenebiguanide, alexidine, polyquaternium-1, hexetidine, bronopol and a very low concentration of hydrogen peroxide, e.g.,, 50 to 200 ppm.

The solutions of the invention are compatible with both rigid gas permeable and hydrophilic contact lenses during cleaning, wetting, soaking, rinsing and disinfection.

One embodiment of the invention is a combination of dry, solid, water soluble or dispersible unit dosage forms, eg. tablets. One type of tablet would contain the tromethamine or salt thereof, the microbicide, and the chelating agent. Prior to use, the tablet is dissolved in the diluent, eg. water or saline to form a solution for disinfecting contact lenses. Another embodiment would be an aqueous solution comprising the novel disinfecting ingredients.

A typical aqueous solution of the present invention may contain additional ingredients which would not affect the basic and novel characteristics of the active ingredients described earlier, such as tonicity agents, surfactants and viscosity inducing agents, which may aid in either the lens cleaning or in providing lubrication to the eye. Suitable tonicity agents include sodium chloride, potassium chloride, glycerol or mixtures thereof. The tonicity of the solution is typically adjusted to approximately 240–310 milliosmoles per kilogram solution (mOsm/kg) to render the solution compatible with ocular tissue and with hydrophilic contact lenses. In one embodiment, the solution contains 0.01 to 0.5 weight percent sodium chloride.

Suitable surfactants include tyloxapol, which is 4-(1,1,3,3-tetramethylbutyl)phenol polymer with formaldehyde and oxirane; pluronic ® or poloxamers, nonionic block copolymer surfactants which are block copolymers of propylene oxide and ethylene oxide; octoxynol or octyphenoxy polyethoxyethanol prepared by reacting isooctylphenol with ethylene oxide; poloxamine which is a block copolymer derivative of ethylene oxide and propylene oxide combined with ethylene diamine; and nonoxynol nonionic surfactant mixtures prepared by reacting nonylphenols with ethylene oxide. Most of these surfactants am described in the Merck Index, supra. The surfactants can be employed in amounts ranging from about 0.0001 to about 20% by weight, preferably from about 0.005 to about 5.0% by weight, more preferably from about 0.025 to about 1 percent by weight. In one embodiment 250 ppm of tyloxapol is used.

Suitable viscosity inducing agents can include lecithin or the cellulose derivatives such as hydroxymethylcellulose, hydroxypropylcellulose and methylcellulose in amounts similar to those for surfactants, above.

If solid dosage forms are used, the formulations may include conventional lubricants, binders, and excipients which include, but are not limited to glycerol, sorbitol, propylene glycol, polyethylene glycols and dextran. These materials are used in amounts varying between 0.001 and 30% by weight, preferably between about 0.1 and 5 percent.

The preferred aqueous solutions of the invention can be prepared by adding the ingredient as follows. Add the tromethamine to water. Adjust the pH of the solution to a pH from about 6.8 to about 7.8. Add the chelating agent and the tonicity agent, if required. Stir to dissolve the above ingredients. Optionally, add the surfactant and the viscosity inducing agent. Add the microbicide. The final product can be rendered sterile by sterile filtration, heat sterilization or a combination thereof.

A suggested method for disinfecting a contact lens is as follows. The lenses are first rubbed with a few drops of the subject solution or saline and rinsed to remove surface contaminants such as mucous, eye makeup, etc., and then placed in a suitable container with a sufficient amount of the aqueous solution to cover the lenses. The lenses are allowed to soak for at least 10 minutes and up to 8 hours to achieve substantial kill of the microorganisms. The foregoing method is carded out at ambient or at elevated temperatures, ie. 20° C. to about 100° C.

To illustrate the manner in which the invention may be carried out, the following examples are given. It is understood, however, that the examples are for the purposes of illustration and the invention is not to be regarded as limited to any of the specific materials or conditions set forth therein. The term "q.s." means quantum sufficiat or "a sufficient volume"—to bring the aqueous solution to volume. Unless otherwise stated, "%" means weight per unit volume expressed as a percent "(w/v)."

The disinfecting efficacy was determined by inoculating the test solution with a microbial suspension at a final concentration of approximately $10^6$ colony forming units per ml. Each inoculated solution was then vigorously agitated and kept at ambient temperature.

At various times after inoculation each solution was vigorously agitated and one mi. aliquots withdrawn and dispensed into 9 ml of neutralizing broth. Ten-fold serial dilutions of each inoculated solution were prepared in neutralizing broth. The solutions were plated out at effective dilutions of 1/10th to 1/100,000th on nutrient agar with or without neutralizing agents. The plates were incubated under optimal conditions of time and temperature for growth and the colonies counted.

The concentration of the survivors and the log reductions were calculated. Each ten-fold decrease in concentration constitutes a one-log reduction.

EXAMPLE 1

This example illustrates the surprising efficacy of tromethamine in an isotonic aqueous solution as a microbicide that is effective against difficult-to-kill organisms.

| Example 1A: | Isotonic aqueous solution containing tromethamine. |
| --- | --- |
| Tromethamine | 1.2% |
| Sodium Chloride | 0.3% |
| HCl | q.s. ad pH of 7.4 |
| Purified Water USP | q.s. ad 100 ml. |
| Example 1B: | Isotonic solution containing tromethamine and chelating agent. |
| Tromethamine | 1.2% |
| Sodium Chloride | 0.3% |
| Disodium EDTA | 0.05% |
| HCl | q.s. ad pH of 7.4 |
| Purified Water USP | q.s. ad 100 ml. |

Both tromethamine solutions are prepared by dissolving the ingredients in water, adjusting the pH with hydrochloric acid and bringing to volume with additional water. Each solution is sterilized using a 0.22 micron filter.

| Example 1C (Comparative): | Isotonic borate solution. |
|---|---|
| Boric Acid | 1.03% |
| Sodium Borate | 0.19% |
| Sodium Chloride | 0.3% |
| Purified Water USP | q.s. ad 100 ml. |

| Example 1D (Comparative): | Isotonic borate solution and chelating agent. |
|---|---|
| Boric Acid | 1.03% |
| Sodium Borate | 0.19% |
| Sodium Chloride | 0.3% |
| Disodium EDTA | 0.05% |
| Purified Water USP | q.s. ad 100 ml. |

Both borate solutions are prepared by dissolving the ingredients in water and bringing to volume with additional water, The pH of the solution is 7.4. Each solution is sterilized by filtering through a 0.22 micron filter.

| Example 1E (Comparative): | Isotonic phosphate solution. |
|---|---|
| Sodium Dihydrogen Phosphate | 0.16% |
| Disodium Hydrogen Phosphate | 0.757% |
| Sodium Chloride | 0.44% |
| Purified Water USP | q.s. ad 100 ml. |

| Example 1F (Comparative): | Isotonic phosphate solution and chelating agent. |
|---|---|
| Sodium Dihydrogen Phosphate | 0.16% |
| Disodium Hydrogen Phosphate | 0.757% |
| Sodium Chloride | 0.44% |
| Disodium EDTA | 0.05% |
| Purified Water USP | q.s. ad 100 ml. |

Both phosphate solutions were prepared by dissolving the ingredients in water and adjusting to volume with additional water. The pH of the solution is 7.4. The formulation for the phosphate solution without chelator is identical to that listed in the USP for isotonic ophthalmic saline. The solutions were sterilized by filtering through a 0.22 micron filter.

When tested for disinfecting efficacy, the following results were achieved:

| Example | Log Reduction at Four Hours | |
|---|---|---|
| | S. marcescens | C. albicans |
| 1A (This invention) | 2.6 | 1.4 |
| 1B (This invention) | 4.9 | 1.9 |
| 1C (Comparative) | 0.5 | <0.1 |
| 1D (Comparative) | 0.7 | <0.1 |
| 1E (Comparative) | 0.8 | <0.1 |
| 1F (Comparative) | 0.7 | <0.1 |

As can be seen, isotonic aqueous solutions containing 1.2% tromethamine reduced the concentrations of two difficult-to-kill organisms by a factor of greater than 10. Furthermore, tromethamine has a synergistic effect when combined with a chelating agent, disodium EDTA. In contrast, isotonic aqueous solutions containing borate and phosphate buffer systems, with or without disodium EDTA, have significantly less disinfection efficacy.

Example 2
This example illustrates the disinfection properties of various formulations within the scope of this invention.

| Ex. No. | Tromethamine % WV | DiNa EDTA % WV | PHMB (PPM) | Onamer M (PPM) | Polybrene (PPM) | Tyloxapol (PPM) | Hexetidine (PPM) | CG (PPM) | AH (PPM) |
|---|---|---|---|---|---|---|---|---|---|
| 2a | 0.5 | 0.05 | — | 5 | — | — | — | — | — |
| 2b | 0.5 | 0.05 | — | — | 5 | — | — | — | — |
| 2c | 1.2 | 0.05 | 1 | — | — | — | — | — | — |
| 2d | 1.2 | 0.05 | 1 | — | — | 5 | — | — | — |
| 2e | 1.2 | 0.05 | 1 | — | — | — | 15 | — | — |
| 2f | 1.2 | 0.05 | 1 | — | — | — | 10 | — | — |
| 2g | 1.2 | 0.05 | — | — | — | — | — | 50 | — |
| 2h | 1.2 | 0.05 | — | — | — | — | — | — | 50 |
| 2i | 1.2 | 0.10 | — | — | — | — | — | 10 | — |

In the above table:
DiNaEDTA is disodium EDTA.
PHMB is polyhexamethylene biguanide hydrochloride salt, a microbicide.
Onamer M TM, Polybrene TM, and Hexetidine TM, are microbicides.
CG is chlorhexidine gluconate, a microbicide
AH is alexidine hydrochloride, a microbicide
Tyloxapol is a surfactant.
In addition to the above-listed ingredients, each solution contained 0.37% Na Cl for isotonicity and the pH of each solution was adjusted to 7.4 with HCl.
Following are log reductions for various organisms after 4 hours.

| Ex. No. | S.m. | S.e. | C.a. | A.n. | A.f. |
|---|---|---|---|---|---|
| 2a | 5.4 | >5.3 | — | — | — |
| 2b | 2.3 | 3.6 | — | — | — |
| 2c | >6.8 | — | — | — | 1.1 |
| 2d | >6.8 | — | — | — | 1.3 |
| 2e | — | — | — | — | 1.6 |
| 2f | — | — | — | — | 1.3 |
| 2g | — | — | >5.7 | 2.0 | — |
| 2h | — | — | >5.7 | 1.2 | — |
| 2i | >6.1 | — | — | 1.1 | — |

S.m is *Serratia marcescens*
S.e. is *Staphylococcus epidermidis*
C.a. is *Candida albicans*
A.n. is *Aspergillus niger*
A.f. is *Aspergillus fumigatus*

EXAMPLE 3

This example compares the disinfection ability of a preferred formulation of this invention prepared in a manner suitable for making commercial quantities, with two commercial solutions.

Solution 3A

A commercial solution tradenamed Optifree; described in its package insert as "a sterile, buffered, isotonic, aqueous solution containing a citrate buffer and sodium chloride with edetate disodium 0.05% and POLYQUAD ®* (polyquaternium-1) 0.001% as preservatives."

Solution 3B

A commercial solution tradenamed ReNu ® Multi-Purpose Solution described in its package insert as "A sterile, isotonic solution that contains boric acid, poloxamine, sodium borate, and sodium chloride; preserved with DYMED ™ (polyaminopropyl biguanide) 0.00005% and edetate disodium 0.1%.

Solution 3C (This invention)

| | |
|---|---|
| Tromethamine | 1.2% |
| Disodium edetate | 0.05% |
| NaCl | 0.37% |
| Tyloxapol | 0.025% |
| Polyhexamethylene biguanide, HCl salt | 0.0001% |
| Hydrochloric acid | adjust to pH 7.5 ± 0.2 |
| USP Purified Water | q.s. ad 100% |

Tromethamine, disodium edetate and sodium chloride were dissolved in a portion of the water and the pH was adjusted to 7.5±0.2 using 2.5N Hydrochloric acid. Tyloxapol and polyhexamethylene biguanide hydrogen chloride salt were added and allowed to dissolve. The solution was adjusted to volume with purified water. The solution was sterilized through a 0.22 micron sterilizing filter.

Comparative disinfection results are given in the following table. All tests for a particular microorganism were performed on the same day, thereby eliminating the inaccuracies sometimes caused by day-to-day variations in the activity of microorganisms from the same source. Differences in log reductions of less than 0.5 logs are considered to be within experimental error.

| | Log Reduction (4 hours) Solution No. | | |
|---|---|---|---|
| Microorganism | 3A | 3B | 3C |
| *Pseudomonas aeruginosa* (Pa) | 3.7 | 4.7 | ≧6.7 |
| *Pseudomonas cepacia* (Pc) | 0.2 | 2.2 | 3.2 |
| *Pseudomonas diminuta* (Pd) | 1.2 | 5.5 | 5.5 |
| *Pseudomonas fluorescens* (Pf) | 0.7 | 4.8 | 5.7 |
| *Staphylococcus epidermidis* (Se) | ≧6.5 | ≧6.5 | ≧6.5 |
| *Serratia marcescens* (Sm) | 1.8 | ≧5.5 | ≧5.5 |
| *Candida albicans* (Ca) | 0.0 | 3.1 | 2.2 |
| *Aspergillus fumigatus* (Af) | 0.5 | 0.4 | 0.5 |
| *Aspergillus niger* (An) | 0.0 | 0.0 | 0.0 |
| *Acinetobacter calcoaceticus* (Ac) | 2.3 | 4.1 | 4.8 |
| *Bacillus cereus* (Bc) | 3.8 | 3.9 | 4.1 |
| *Bacillus pumilus* (Bp) | 3.0 | 2.9 | 2.9 |
| *Cornybacterium xerosis* (Cx) | 4.9 | 2.8 | 2.5 |
| *Enterobacter cloacea* (Ec) | 5.8 | 5.9 | 5.5 |
| *Enterococcus faecalis* (Ef) | 2.9 | 5.8 | 4.4 |
| *Micrococcus luteus* (Ml) | 4.8 | 5.0 | 5.4 |
| *Proteus mirabilus* (Pm) | 2.9 | 3.1 | 4.3 |
| *Candida parapsilosis* (Cp) | 0.3 | 5.0 | 4.3 |
| *Fusarium solani* (Fs) | 4.2 | 6.2 | 6.2 |

Pseudomonas species are very virulent and are highly implicated in ocular infections related to contact lens wear. For the four Pseudomonas species in the above table, the disinfectant of the present invention was superior for three species and superior to solution 3A, but equal to solution 3B, for the fourth species.

For other bacteria and fungi implicated in contact lens wear such as Se, Sm, Ca, Af, Bc, Fs, and Cp, the solution of this invention is equal to or better than 3A or B in five of the seven examples and in the other two fungal organisms Ca and Cp, significant reduction (greater than 99.4% based on a $10^6$ inoculum) was observed.

For the other organisms tested which are pathogens but not generally implicated in the eye, the test results demonstrated substantially equal performance.

Based on the above analysis, it is clear that the present invention provides inventive methods and compositions for disinfecting contact lenses.

EXAMPLE 4

Alternative contact lens cleaning/disinfecting solution

| | |
|---|---|
| 1.2% | Tromethamine/Tromethamine Hydrochloride (pH = 7.2) |
| 0.05% | Disodium Edetate |
| 0.37% | Sodium Chloride |
| 0.01% | Tyloxapol |
| 0.0001% | Polyhexamethylene Biguanide, hydrochloride |
| q.s. | Purified water, U.S.P. |

EXAMPLE 5

This example illustrates the synergistic anti-microbial effect of the present invention for very low concentrations of peroxide.

| Ex. No. | Tris % WN | Di Na EDTA % WN | $H_2O_2$ PPM | Log Reduction (4 Hr) | | |
|---|---|---|---|---|---|---|
| | | | | Sm | Se | Ca |
| 5A | 1.2 | 0.05 | 50 | >5.8 | 5.3 | |
| 5B | 1.2 | 0.05 | 50 | >6.4 | — | >5.9 |
| 5C | (Comparative, see below) | | | 1.5 | 0.8 | — |
| 5D | (Comparative, see below) | | | 1.9 | — | 5.3 |

The solution for example 5C was Software Saline ® a CibaVision product.

The solution for example 5D was AOSept ® diluted with Unisol ® saline to 0.1% $H_2O_2$.

We claim:

1. A method for disinfecting a contact lens comprising contacting the lens with an isotonic aqueous solution comprising 0.6 to 2 weight percent tromethamine component selected from the group consisting of tromethamine, ophthalmologically acceptable salts thereof and mixtures thereof for a time sufficient to disinfect the lens.

2. The method of claim 1 wherein the solution comprises 0.8 to 1.5 weight percent of the tromethamine component.

3. The method of claim 1 or claim 2 wherein the contacting is effective to reduce the concentration of microorganisms selected from *S. marcescens*, *C. albicans* or both present on the lens prior to the contacting.

4. The method of claim 1 wherein the solution further comprises from 0.01 to 1 weight percent of an ophthalmologically acceptable chelating agent.

5. The method of claim 4 wherein the chelating agent is disodium EDTA.

6. The method of claim 1 wherein the solution includes an additional microbicide comprising 0.00001 to 0.01 weight percent of a microbicide selected from the group consisting of PHMB, N-alkyl-2-pyrrolidone, chlorhexidine, polyquaternium-1, hexetidine, bronopol, alexidine, very low concentration of peroxide, ophthalmologically acceptable salts thereof and mixtures thereof.

7. The method of claim 6 wherein the additional microbicide is selected from the group consisting of PHMB, ophthalmologically acceptable salts thereof and mixtures thereof.

8. A contact lens disinfecting solution comprising:
(a) 0.6 to 2 weight percent of a first microbicide comprising tromethamine component selected from the group consisting of tromethamine, ophthalmologically acceptable salts thereof and mixtures thereof;
(b) 0.01 to 1 weight percent of an ophthalmologically acceptable chelating agent;
(c) 0.00001 to 0.01 weight percent of a second microbicide selected from the group consisting of PHMB, N-alkyl-2-pyrrolidone, chlorhexidine, polyquaternium-1, hexetidine, bronopol, alexidine, from 50 to 200 ppm hydrogen peroxide, ophthalmologically acceptable salts thereof, and mixtures thereof;
(d) 0.01 to 0.5 weight percent sodium chloride; and
(e) water q.s. 100%, said contact lens disinfecting solution having an ocularly compatible pH.

9. The contact lens disinfecting solution of claim 8 comprising:
1.2 weight percent of said first microbicide;
0.05 weight percent of said ophthalmologically acceptable chelating agent;
1 ppm of said second microbicide;
HCl q.s. pH of 7.3 to 7.7;
0.0001 to 20 weight percent of a surfactant;
0.37 weight percent sodium chloride; and water q.s. 100 percent.

10. The contact lens disinfecting solution of claim 8 or 9 wherein said ophthalmologically acceptable chelating agent comprises disodium EDTA.

11. The contact lens disinfecting solution of claim 9 wherein said second microbicide is selected from the group consisting of PHMB, ophthalmologically acceptable salts thereof, and mixtures thereof.

12. The contact lens disinfecting solution of claim 10 wherein said surfactant comprises 250 ppm of tyloxapol.

13. The method of claim 2 wherein the solution further comprises from 0.01 to 1 weight percent of an ophthalmologically acceptable chelating agent.

14. The method of claim 3 wherein the solution further comprises from 0.01 to 1 weight percent of an ophthalmologically acceptable chelating agent.

15. The contact lens disinfecting solution of claim 8 wherein said first microbicide is present in an amount of 0.8 to 2 weight percent.

16. The contact lens disinfecting solution of claim 8 wherein said second microbicide is selected from the group consisting of PHMB, ophthalmologically acceptable salts thereof, and mixtures thereof.

17. The contact lens disinfecting solution of claim 10 wherein said second microbicide is selected from the group consisting of PHMB, ophthalmologically acceptable salts thereof, and mixtures thereof.

18. A contact lens disinfecting solution comprising:
(a) 0.6 to 2 weight percent of tromethamine;
(b) 0.01 to 1 weight percent of disodium EDTA;
(c) 0.00001 to 0.1 weight percent of a component selected from the group consisting of PHMB, ophthalmologically acceptable salts thereof and mixtures thereof;
(d) 0.005 to 5.0 weight percent of tyloxapol;
(e) sodium chloride in an amount effective to render said contact lens disinfecting solution isotonic; and
(f) water q.s. 100 percent, said contact lens disinfecting solution having an ocularly compatible pH.

19. The contact lens disinfecting solution of claim 18 having a pH between 6.8 and 7.8.

20. The contact lens disinfecting solution of claim 18 which contains 1.2 weight percent tromethamine, 0.05 weight percent disodium EDTA, 0.0001 weight percent component (c) and 0.025 weight percent tyloxapol.

* * * * *

UNITED STATES PATENT AND TRADEMARK OFFICE
CERTIFICATE OF CORRECTION

PATENT NO. : 5,422,073
DATED : June 6, 1995
INVENTOR(S) : Mowrey-Mckee et al

It is certified that error appears in the above-indentified patent and that said Letters Patent is hereby corrected as shown below:

Column 3, line 51; delete "am" and insert in place thereof --are--.

Column 4, line 37; delete "mi" and insert in place thereof --ml.--.

Column 8, line 37; delete "WN" and insert in place thereof --w/v--.

Signed and Sealed this

Seventh Day of January, 1997

Attest:

BRUCE LEHMAN

Attesting Officer

Commissioner of Patents and Trademarks